(12) United States Patent
Alghamdi

(10) Patent No.: US 9,616,095 B2
(45) Date of Patent: Apr. 11, 2017

(54) METHOD AND A COMPOSITION HAVING PROPHYLACTIC ACTIVITY AGAINST VENOMS AND TOXINS

(71) Applicant: UMM AL-QURA UNIVERSITY, Makkah (SA)

(72) Inventor: Saeed Saeed Alghamdi, Makkah (SA)

(73) Assignee: Umm Al-Qura University, Makkah (SA)

( * ) Notice: Subject to any disclaimer, the term of this patent is extended or adjusted under 35 U.S.C. 154(b) by 303 days.

(21) Appl. No.: 14/404,710

(22) PCT Filed: Nov. 17, 2014

(86) PCT No.: PCT/IB2014/002463
§ 371 (c)(1),
(2) Date: Dec. 1, 2014

(87) PCT Pub. No.: WO2016/079553
PCT Pub. Date: May 26, 2016

(65) Prior Publication Data
US 2016/0136226 A1    May 19, 2016

(51) Int. Cl.
*A01N 65/00* (2009.01)
*A61K 36/889* (2006.01)
*A61K 9/00* (2006.01)

(52) U.S. Cl.
CPC .......... *A61K 36/889* (2013.01); *A61K 9/0053* (2013.01); *A61K 9/0095* (2013.01)

(58) Field of Classification Search
CPC .................................................... A61K 36/00
USPC ....................................................... 424/725
See application file for complete search history.

(56) References Cited

FOREIGN PATENT DOCUMENTS

| DE | 10 2011 009 719 A1 | 8/2011 |
|---|---|---|
| WO | WO 2006/131932 A1 | 12/2006 |
| WO | 2007 107787 | 9/2007 |

OTHER PUBLICATIONS

Tirmidhi, H., "Muhammad and Poison", URL: http://www.answering-islam.org/Shamoun/muhammad_poison.htm pp. 1-5, (Jan. 8, 2014).
International Search Report and Written Opinion issued Apr. 30, 2015 in PCT/IB2014/002463.
Arshad H. Rahmani, et al., "Review Article Therapeutic effects of date fruits (Phoenix dactylifera) in the prevention of diseases via modulation of anti-inflammatory, anti-oxidant and anti-tumour activity" Int J Clin Exp Med, vol. 7, No. 3, XP055183610, Jan. 1, 2014, pp. 483-491.
Abdul-Karim J. Sallal, et al., "Inhibition of haemolytic activity of snake and scorpion venom by date extract" Biomedical Letters, The Faculty Press, vol. 55, No. 217, XP009183794, Jan. 1, 1997, pp. 51-56.
Emna Behija Saafi, et al., "Protective effect of date palm fruit extract (Phoenix dactylifera L.) on dimethoate induced-oxidative stress in rat liver" Experimental and Toxicologic Pathology, vol. 63, No. 5, XP009149528, Jul. 1, 2011, pp. 433-441.
Bashar Saad, et al., "Safety of Traditional Arab Herbal Medicine" Evidence-Based Complementary and Alternative Medicine, vol. 3, No. 4, XP009149529, Sep. 7, 2006, pp. 433-439.
Muhammad T. Khan, et al., "Evaluation of Seeds of Phoenix sylvestris as Novel Candidate Adsorbent in Paracetamol Poisoning" Acta Farmaceutica Bonaerense, vol. 31, No. 5, XP009183817, Jun. 1, 2012, pp. 678-685.

*Primary Examiner* — Michael Meller
(74) *Attorney, Agent, or Firm* — Oblon, McClelland, Maier & Neustadt, L.L.P.

(57) ABSTRACT

A composition to be administered to a patient to prevent harmful effects of biological venom or chemical toxin is described. The composition includes the use of the date palm, *Phoenix dactylifera* fruit to be administered to a patient at a particular dosage that effectively prevents the patient from the effects of exposure to a biological venom or a chemical toxin.

4 Claims, No Drawings

METHOD AND A COMPOSITION HAVING PROPHYLACTIC ACTIVITY AGAINST VENOMS AND TOXINS

BACKGROUND OF THE DISCLOSURE

Technical Field

The present disclosure relates to a composition comprising the fruit *Phoenix dactylifera* and/or an active ingredient derived therefrom and a method for administering the composition to a subject to inhibit effects from exposure to a biological venom or a chemical toxin.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Dates, the fruit of the date palm *Phoenix dactylifera* are virtually fat, cholesterol and sodium free. They provide essential vitamins and minerals—such as B-complex vitamins, magnesium and iron. They also contain fiber as an insoluble component. Dates provide a wide range of essential nutrients, and are a very good source of dietary potassium. The sugar content of ripe dates is about 80% while the remainder consists of protein, fiber, and trace elements including boron, cobalt, copper, fluorine, magnesium, manganese, selenium, and zinc. The glycemic index for three different varieties of dates are 35.5 (khalas), 49.7 (barhi) and 30.5 (bo ma'an). The caffeic acid glycoside 3-O-caffeoyl-shikimic acid (also known as dactylifric acid) and its isomers, are enzymic browning substrates found in dates.

The fruit of the date palm (*Phoenix dactylifera*), because of its tannin content, has been used in traditional medicines as a detersive and astringent in the treatment of intestinal disorders. Dates have also been used in the form of an infusion, decoction, syrup or paste to alleviate the symptoms of sore throat, colds and bronchial catarrh. Dates have also been said to counteract alcohol intoxication.

The Al-Ajwah is a palm tree cultivated in the Madinah region of the Kingdom of Saudi Arabia. The Al-Ajwah tree produces *Phoenix dactylifera* having physiologically useful properties. Specifically, the Ajwah date has anti-inflammatory properties similar to commercially available drugs like ibuprofen and aspirin. The inhibition rate in Ajwah is equal to existing commercial anti-oxidant products available in the market. The dark brown Ajwah date from the Madinah region of the Kingdom of Saudi Arabia is known for its softness, dryness and high price in the Kingdom's date market. According to health experts, Ajwah dates contain many flavonoid glycosides, which have anti-oxidant properties. Beyond the anti-oxidant and anti-inflammatory benefits, the sugar in Ajwah dates is only monosaccharaides, making the date beneficial for people who suffer from Type 2 diabetes. Ajwah dates are also found to have a cyclooxygenase inhibitory effect that is similar to commercial anti-inflammatory drugs like aspirin, ibuprofen, celebrex and naproxen. Ajwah dates contain potassium. Potassium is beneficial for controlling diarrhea. They are easily digestible, which helps to cope with the problems of diarrhea and food poison. Ajwah dates have a high content of iron which makes them great home remedies for reducing iron deficiency. Anemic patients are advised to eat several dates on a daily basis to raise their level of iron in the blood and dates are also helpful in increasing hemoglobin levels in the body.

Dates are of course also widely used as foodstuffs, and it is known to produce date pastes and date preserves, e.g. for use in bakery products and confectionery. However, the fibrous nature of the date material, and the presence of insoluble material within the dates, means that such preparations are generally rather inhomogeneous, have a poor mouth feel, and are difficult to formulate into a pharmaceutically acceptable liquid or compress into a tablet. Dates have been used to produce various date juice products. These are often clear or clarified liquids, containing only soluble components of the date. However, such products have found little use, due to their rather poor and bland taste. Attempts have also been made to prepare date-based beverages.

Some of these beverages have been carbonated, some not, but generally they have required reinforcement with organic acids and additional flavors in order to produce acceptable tasting products. Date syrups have also been produced, but again they comprise substantially only the soluble components of the dates, and are produced by extraction of the date juice, clarification and concentration. Date spread is also known, and fits between date paste, made of the whole date flesh, and date syrup, from which all non-solubles have been removed.

Conventional preparations of dates have characteristics different from modern medicines, such as elegance, consistency, reproducible quality, safety, physical, chemical and microbiological stability and bioavailability. There is a dearth of clinical evidence of efficacy or reports of any clinical trials carried out to demonstrate efficacy of dates in the aforementioned or any other ailments. One possible reason for the lack of clinical trials is that there are, at present, no reliable, stable, safe, convenient and pharmaceutically acceptable preparations of dates. Useful oral liquid and solid dosage forms of dates have yet to be thoroughly described.

BRIEF SUMMARY OF THE DISCLOSURE

In one embodiment, the disclosure relates to a method for prophylactically administering a composition comprising the fruit *Phoenix dactylifera* to a subject an amount effective to inhibit or prevent a biological toxin or a chemical toxin from causing harm.

In another embodiment the method comprises administering a composition comprising the fruit *Phoenix dactylifera* to a subject in an amount effective to inhibit or prevent a biological toxin or a chemical toxin from causing harm.

In another embodiment the method comprises homogenizing the fruit *Phoenix dactylifera*.

In another embodiment the method comprises dissolving or suspending the homogenized fruit to an aqueous solution to form a composition.

In another embodiment the method comprises administering the composition to a subject in an amount of at least 0.4 g/kg.

In another embodiment the method comprises administering the composition to a subject in an amount of at least 0.8 g/kg and effective to provide prophylactic protection from harm caused by a biological toxin or a chemical toxin.

In another embodiment the composition prevents the harmful effects of one or more biological toxins including venoms deriving from spiders, snakes, scorpions, jellyfishes, wasps, bees, ants, termites, honeybees, wasps, poison dart frogs.

In another embodiment the composition prevents the harmful effects of one or more chemical toxins including carbon tetrachloride, strychnine, cyanide, lead, arsenate and mercury.

In another embodiment the homogenized date fruit is administered orally in solid or liquid form.

In another embodiment the composition in liquid form further includes syrup, artificial sweetening agents, or natural fruit flavoring agents.

In another embodiment the patient is administered the composition only if no food has been ingested for a time period of 12 hours.

In another embodiment the subject is any mammal including a human.

Another embodiment of the disclosure relates to a method for inhibiting a biological toxin or a chemical toxin in a subject comprising administering a composition comprising the fruit *Phoenix dactylifera* to a subject in an amount effective to inhibit the effects of the toxin.

Exemplary implementations of the present disclosure include:

A: A method for administering a homogenized composition comprising the fruit *Phoenix dactylifera* in an amount effective to prophylactically inhibit a biological toxin or a chemical toxin from causing harm to a mammal, comprising:

administering the homogenized composition in an amount of at least 0.4 g of date/kg of the mammal.

B: The method of A, further comprising:
homogenizing the fruit *Phoenix dactylifera*.

C: The method of A, wherein the fruit *Phoenix dactylifera* is the Ajwah date.

D: The method of A, wherein the composition is administered in an amount effective to prophylactically prevent harm from:

one or more biological toxins selected from the group consisting of spider venom, snake venom, scorpion venom, jellyfish venom, bee venom, ant venom, termite venom, honeybee venom, wasp venom, and poison dart frog venom.

E: The method of A, wherein the composition is administered in an amount effective to prophylactically prevent harm from:

one or more chemical toxins selected from the group consisting of carbon tetrachloride, strychnine, cyanide, lead, arsenate, and mercury.

F: The method of A, wherein the composition is administered orally in solid or liquid form.

G: The method of A, wherein the composition is administered in the liquid form and wherein the homogenized composition includes:

syrup;
artificial sweetening agents; or
natural fruit flavoring agents.

H: The method of A, wherein the patient is administered the composition only if no food has been ingested for a time period of 12 hours.

I: The method of A, wherein the mammal is a human.

J: The method of A wherein the composition is administered in an amount of 0.70 g/kg-0.95 g/kg to a human.

K: A method of inhibiting a biological toxin or a chemical toxin in a subject, comprising:

administering a homogenized composition comprising a date fruit in an amount of at least 0.4 g of date/kg of the subject;

wherein the administering occurs at a time period of at least 12 hours before the subject is exposed to the biological toxin or the chemical toxin.

L: The method of K, wherein the subject is any mammal including a dog, horse, or human.

M: The method of K, further comprising:
homogenizing the fruit *Phoenix dactylifera*.

N: The method of K, wherein the fruit *Phoenix dactylifera* is the Ajwah date.

O: The method of K, wherein the composition is administered in an amount effective to inhibit:

one or more biological toxins selected from the group consisting of spider venom, snake venom, scorpion venom, jellyfish venom, bee venom, ant venom, termite venom, honeybee venom, wasp venom, and poison dart frog venom.

P: The method of K, wherein the composition is administered in an amount effective to inhibit:

one or more chemical toxins selected from the group consisting of carbon tetrachloride, strychnine, cyanide, lead, arsenate, and mercury.

Q: The method of K, wherein the composition is administered orally in solid or liquid form.

R: The method of K, wherein the composition is administered in the liquid form and wherein the homogenized composition includes:

syrup;
artificial sweetening agents; or
natural fruit flavoring agents.

S: The method of K, wherein the mammal is a human.

T: The method of K, wherein the composition is administered in an amount in the range of 0.70 g/kg-0.95 g/kg to a human.

The foregoing paragraphs have been provided by way of general introduction, and are not intended to limit the scope of the following claims. The described embodiments, together with further advantages, will be best understood by reference to the following detailed description.

DETAILED DESCRIPTION OF THE EMBODIMENTS

The present disclosure relates to a composition that may be prophylactically administered to a patient in an amount effective to prevent the damaging effects of a biological or chemical toxin or poison once the toxin or poison is introduced to the patient's immune system.

The composition includes components obtained from the fruit *Phoenix dactylifera*, a date. Any suitable variety of date may be of utility in the present disclosure including but not limited to Ajwah dates, deglet noor dates, halawy dates, khadrawy dates, zahidi dates, thoory dates, or medjool dates. It is possible to use dates at all stages of ripening, but it is preferred to use the Ajwah date at a khalal stage, when the Ajwah date reaches the maximum stage of ripening.

In one embodiment of the disclosure the composition is effective against biological toxins or biotoxins that are introduced to a patient's immune system including but not limited to toxins and venoms deriving from spiders, snakes, scorpions, jellyfishes, bees, ants, termites, honeybees, wasps, poison dart frogs. Preferably the composition is effective against biological toxins or biotoxins that are introduced to a patient's immune system deriving from the following species: *Naja Melanoleuca, Bitis Gabonica, Bitis Arietans*, Narrow-banded krait (*Bungarus multicinctus*), Cobra snake (*Naja naja atra* Chinese Cobra), King cobra (*Ophiophagus hannah*), *Agkistrodon acutus, Vipera russelli, Siamensis* smith, *Bungarus fasciatus* Schneider, *Agkistrodon blomhoffi* Boie, *Trimeresurus mucroquamatus, Trimerurus stejnegeri* Schmidt, *Acanthopis laevis, Hadogenes troglodytes, Leiurus quinquestriatus*.

Chemical toxins include but are not limited to carbon tetrachloride, strychnine, cyanide, lead, arsenate and mercury.

Venoms derived from a variety of animals are complex biological mixtures of upwards of 50 compounds, mostly proteins and polypeptides. A complex mixture of proteins, enzymes, and various other substances with toxic and lethal properties serve to immobilize an animal that is the target of the venom. Enzymes, which when injected into an animal, start tissue digestion. Death from a toxic bite is due to respiratory or circulatory failure caused by various neurotoxins, cardiotoxins (also called cytotoxins), coagulation factors, and other substances acting alone or synergistically caused from the proteins in the venom. The venoms thus contain substances designed to affect the vital processes such as nerve and muscle function, the action of the heart, circulation of the blood and the permeability of membranes. Most constituents of venoms are proteins, but low molecular weight compounds such as peptides, nucleotides and metal ions are also present.

In another embodiment the composition described in the present disclosure prevents the venom from fatally or catastrophically affecting muscle and nerve function, action of the heart, circulation of the blood and permeability of membranes once the venom enters a patient's body.

In another embodiment of the disclosure the composition is effective for preventing the harmful effects of compositions found in venom including but not limited to protein toxins, protein neurotoxins, enzymes including but not limited to hydrolytic enzymes, digestive hyrdolases, L-amino acid oxidases, phospholipases, kallikrein-like serine proteases, metalloproteinases, phosphodiesterases, phospholipase A2, amino acid oxidases, proteases hyaluronidase and polypeptide toxins including but not limited to cytotoxins, cardiotoxins, postsynaptic neurotoxins, α-bungarotoxins, α-cobratoxin and any other peptides, lipids, nucleosides, carbohydrates, amines, fasiculins, thrombin-like pro-coagulants, or oligopeptides found in venom.

Harmful effects of compositions found in venom include but are not limited to blood coagulation, blood pressure irregulation, modification in transmission of nervous or muscular impulse, muscular contractions, tetany, paralysis, long term fasciculations, short term fasciculations, numbness, rupturing of cell membranes, irregular heartbeats, death, dismantling of the molecular structure of the area surrounding and including the bite, cell death, neurodegeneration, hemolysis, loss of limb, nausea, disorientation, headaches, increased intracellular protein degradation, and oxidative stress to the brain and other organs in the body.

In another embodiment the date composition is administered in an amount to prevent harm from a biological or chemical toxin such that the amount administered increases the $LD_{50}$ of the biological toxin or chemical toxin increases by at least 30%, preferably at least 50% in comparison to the $LD_{50}$ of a control population exposed to the same chemical or biological toxin but that is not administered the composition.

Liquid and solid date-based formulations with acceptable properties for nutriceutical or pharmaceutical use can be prepared. In one embodiment of the disclosure a liquid or solid formulation that comprises processed dates is suitable for nutriceutical or pharmaceutical use by oral administration.

Liquid preparations are in the form of homogeneous aqueous suspensions or solutions using the whole date (without the stone). Such formulations have acceptable taste and mouthfeel. The solid formulations according to the disclosure may have various forms including but not limited to compressed tablet forms and lozenges. The preparation of a fine and homogenous dispersion of processed dates is important to both solid and liquid formulations.

By "homogeneous" in this context is meant that the particles of date material present in the formulation are sufficiently fine and uniform that the formulation feels smooth in the mouth when presented as liquid or in a solid dose form.

Because of the uniformity and fineness of the dispersion, there is a greater degree of contact between the date particles and the papillae on the tongue. Therefore, the date dispersion of this disclosure exhibits "roundness" of taste particularly for a liquid product. This unique property will also apply to the dried dispersion presented in the form of solid dosage form such as chewable or dispersible tablets.

One embodiment of the disclosure includes the composition in liquid form. Thus, according to a first specific aspect of the disclosure, there is provided a liquid dosage formulation, in the form of a homogeneous dispersion in water of date material in finely divided form.

In such formulations, the nutritional principles are better assimilated. The fineness and uniformity of the dispersion may also lead to significantly improved physical stability. The dispersion is physically stable over a long period and is not prone to separation. If some separation does occur, the homogenized product redisperses easily by simple shaking and reverts to its original homogeneous appearance. There is also a significant reduction or attenuation of the typical "collar" effect (separation and also floating of some suspended particles above the separated fluid, and sediment at the bottom part of the bottle) that is commonly observed with suspension formulations, such as extemporaneously prepared dispersions of fruit juices.

In quantitative terms, "homogeneous" may mean that all or substantially all of the date material is present in the form of particles having a particle size of less than 500 μm, and more preferably less than 100 μm. For instance, more than 90% w/w of the date material is preferably present in the form of particles with a size less than 100 μm, or a size less than 80 μm, or a size less than 50 μm. It may well be that the majority of the date material, e.g. more than 90% w/w or more than 95% w/w, is present in the suspension in the form of particles with a size in the range 1-50 μm.

Preferably, the dates are stoned, but otherwise it is preferred that the date material is whole date material, i.e. substantially the whole of the material that constitutes the flesh of the date, and not just certain components of the date. Soluble components of the date material may dissolve in the aqueous carrier medium, while insoluble components are held in suspension.

In this aspect of the disclosure the amount of dates, on dry basis, will generally be at least 5% w/w, and up to 50% w/w, of the weight formulation, preferably between 5% w/w and 35% w/w, e.g. about 30% w/w of the final weight formulation.

In another embodiment, the dates are administered in a measurement of grams of date per kilograms of patient, in the range of 0.2-0.8 g/kg, 0.3-0.7 g/kg or 0.4-0.6 g/kg of the weight of the solid formulation. Preferably the date composition administered to a patient is at least 0.4 g date composition/kg of patient. More preferably, the date composition administered to a patient is at least 0.8 g date composition/kg of patient.

In one or more embodiments, the date composition is administered in a measurement of milligrams of the date composition per deciliter of blood, at no lower than 50 mg/dL for the date composition to be effective against a toxin, preferably no lower than 100 mg/dL, more preferably no lower than 200 mg/dL.

In at least one embodiment, the date composition is administered to a patient 1-24 hours before exposure to a toxin for the date composition to be effective against the toxin, preferably 1-12 hours, more preferably 1-6 hours.

Once the date composition within concentration ranges specified above is in the bloodstream, it can effectively react against a toxin for the next 24 hours.

Preferably, the date composition is administered to a patient before a meal, for example before breakfast or as breakfast. In other words, a patient should not have any food intake within the last 6 hours before taking the date composition.

The liquid dosage formulation may be prepared by dispersing the date material in water, and subjecting the dispersion to homogenization. Such a process represents a further aspect of the disclosure.

Homogenization of the date dispersion can be achieved by means of a high shear mixer such as a Silverson, which is well known to those skilled in the art. Other forms of colloid mill, fluid energy mill or high pressure homogenization may also be suitable. Conventional techniques such as wet milling, spray-drying and freeze-drying may also be used as part of the process. Additional ingredients of the formulation may be added either before or after homogenizations.

High pressure homogenization is an entirely mechanical process, in which the product is forced by a high pressure piston pump through a homogenizing valve. The commercially available Niro Soavi homogenizer is an example of a suitable high pressure homogenizer.

In the process of homogenization, however performed, the dimensions of the suspended particles of date material are reduced. At the end of the process, the suspension commonly presents a uniform distribution, according to a "Gaussian" curve, although such a particle size distribution may not be essential. The particle size distribution will vary with the operating conditions. The temperature at which dates are dispersed in water prior to or after homogenization and the homogenization pressure may require careful adjustment to achieve a commercially viable, stable, safe and elegant dispersion.

The yield and quality of the dispersion prepared from the dates by homogenization will depend on the variety, ripeness and dimensions of the dates, as well as on the degree of integrity of dates, the manner in which they have been stored, and the preparation technique.

Typically, the steps involved in the production process for homogenization include washing and sorting, dispersing dates in hot or warm water using a high shear mixer, sieving to remove large particles, homogenization, further sieving if necessary, and cooling and filling.

The liquid dosage formulation may include one or more additional nutritional components such as fats, carbohydrates, proteins, vitamins, drugs and minerals.

Fats or lipids that may be incorporated into the liquid formulation include, but are not limited to, coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oil and combinations thereof. Carbohydrates that may be incorporated into the formulation may be simple or complex, lactose-containing or lactose-free, or combinations thereof. Non-limiting examples of suitable carbohydrates include hydrolysed corn starch, maltodexthn, glucose polymers, sucrose, corn syrup, corn syrup solids, rice-derived carbohydrate, glucose, fructose, lactose, high fructose corn syrup and indigestible oligosaccharides such as fructooligosaccharides, and combinations thereof.

The liquid formulation may further comprise any of a variety of vitamins, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

The liquid formulation may further comprise any of a variety of electrolytes, non-limiting examples of which include calcium, phosphorus, magnesium, iron, selenium, manganese, copper, iodine, sodium, potassium, chloride, and combinations thereof.

Another significant aspect of the disclosure relates to use the processed dates dispersion to manufacture solid dosage forms. Thus, according to a second embodiment of the disclosure there is provided a solid formulation suitable for nutriceutical or pharmaceutical use by oral administration, which formulation comprises processed dates.

In solid formulations according to the disclosure, the processed dates may themselves be of nutritional and/or therapeutic value. For instance, the processed dates may have a demulcent effect. Alternatively, the processed dates may function purely as an excipient, in particular as granulating agents, or as an agent capable of improving the palatability of a pharmaceutically active substance with an unpleasant taste. The formulations offer a commercially acceptable, stable, economic, simple, consistent and convenient dosage form for the oral administration of processed dates, either alone or in conjunction with pharmaceutically active agents. Tablets that are dispersed in water prior to administration (e.g. dispersible and effervescent tablets), and also chewable tablets, as are widely used by patients and in particular children, who have difficulty in swallowing conventional tablets or capsules, often contain active ingredients with an unpleasant taste, such as some vitamins and analgesics (e.g. paracetamol). The processed dates used in the present disclosure have a long-lasting flavour and are capable of masking the after taste of such drugs, either alone or in conjunction with other suitable flavours and sweeteners.

The formulation according to the disclosure may take any one of numerous forms. Most preferably, however, the formulation takes the form of a tablet or lozenge. The formulation may be swallowable, disintegratable, effervescent, chewable or suckable, and may be intended for buccal or sub-lingual administration.

Similar to the preparation of the liquid oral dosage form, there may be many methods by which processed dates, usually in finely divided form, may be incorporated into solid dosage forms according to the disclosure. A particularly preferred method, which represents a further aspect of the disclosure, involves the formation of a homogeneous dispersion of the date material in water, mixing of the date dispersion with some or all of the further ingredients of the formulation, and drying to remove excess water.

A typical process for the preparation of tablets in accordance with the disclosure is set out in the following: washing and sorting of date material, dispersion of date material in hot or warm water and homogenization or high shear mixing followed by sieving, further homogenization and final sieving if necessary, granulation (massing) of tablet excipients with homogenized dates granulating agent (dates dispersion). The process of wet massing is carried out in a suitable mixer such as a planetary, high shear mixer or in a fluid bed granulator and includes sieving and drying of granules, further granulation (massing) if necessary with homogenized dates granulating agent (dates dispersion), further sieving and drying of granules, mixing with lubricants, disintegrants and flow aids etc, and compression. In this process, the tablet diluents are granulated with a fine dispersion of dates in water prepared by homogenization and/or milling.

If soluble diluents are required to achieve desired tablet characteristics, then diluent bases such as glucose, sucrose, maltose, lactose, arabinose, xylose, ribose, fructose, mannose, galactose, sorbose, trehalose, sorbitol, xylitol, mannitol, maltitol, lactitol, isomaltol, maltodextrin, hydrogenated starch hydrolysis products and mixtures thereof, and sorbitol are employed for oral, suckable, dispersible, swallowable or chewable tablets.

Alternatively, insoluble diluents, or a mixture of soluble and insoluble excipients, may be granulated with the date dispersion in the manufacturing processes as necessary to achieve the desired properties. Suitable insoluble materials include starches, water-insoluble cellulose derivatives, microcrystalline cellulose or an alkaline earth metal carbonate, sulphate or phosphate.

Lozenges may be prepared by combining sucrose and corn syrup in a ratio of 50% sucrose and 50% corn syrup, 60% sucrose and 40% corn syrup, or 70% sucrose and 30% corn syrup, and incorporating a suitable amount of a dispersion of dates in water. Preferably, the ratio of sucrose and corn syrup is 50% sucrose and 50% corn syrup. In this case, the liquid sucrose syrup and corn syrup and dates are cooked at a temperature in the range of 100-200° C., 110-190° C., or 115-150° C. Preferably the liquid sucrose syrup and corn syrup and dates are cooked at a temperature of 125° C. Final heating is performed, at a temperature in the range of 100-200° C., 110-190° C., or 115-150° C. Preferably the dates are heated at 148° C., under vacuum.

In another embodiment any drugs or herbal ingredients such as liquorice are mixed with other ingredients such as flavors and benzyl alcohol. Any acids, such as citric or tartaric acid, are then mixed. There are many ways of adding the drug and flavors. However the most common method is to add the drug/flavor mixture and other constituents and additives (such as menthol etc.) on the mixing table. The candy base containing dates is then formed, rope-sized, molded, cooled and sized.

In another embodiment chewable tablets may be prepared. The drug and other excipients are granulated using the dates dispersion as a granulating agent to granulate all or some of the ingredients of the composition. Another embodiment includes producing base granules containing one or more diluents produced by granulating with the date dispersion. The base granules are then used for blending and compression with the drug, flavors, sweeteners and other excipients similar to the process used for direct compression.

In another embodiment, if the ingredients are not moisture- and/or heat-sensitive, the drug and other components of the formulation may also be granulated with water containing a binder and/or dates dispersion. These are then sieved, dried and tabletted.

In this aspect of the disclosure the amount of dates, on dry basis, will generally be at least 5% w/w, and up to 50% w/w, preferably between 5% w/w and 35% w/w, eg about 30% w/w of the final weight of the solid formulation. The aqueous dispersion of dates may be used to granulate (where present) diluents, excipients such as disintegrants, flavors, and wetting agents, and the pharmaceutically active agents.

In another embodiment the dates act as an efficient binder, aiding in the compaction of granules and obviating the need to include a conventional binding agent such as Povidone (PVP), as is typically used in tablets prepared by moist granulation.

The formulations according to the disclosure are also of utility for the delivery of pharmaceutically active agents, and in particular are of benefit in the delivery of pharmaceutically active agents that have an unpleasant taste. The longer-lasting taste profile of the homogenized date dispersion is capable of masking the unpleasant taste of a wide range of active agents.

Another embodiment of the invention includes a liquid or solid dosage formulation comprising one or more pharmaceutically active agents, wherein the formulation further comprises processed dates.

The taste-masking effect of the formulation may be further enhanced by the inclusion of additional viscosity enhancing agents, flavours and/or sweeteners.

Flavoring agents that may be used in the present disclosure include, but are not limited to, natural flavors, natural fruit flavors, artificial flavors, artificial fruit flavors, flavor enhancers or mixtures thereof. The natural flavor may be selected from apple essence, pear essence, peach essence, berry essence, wildberry essence, date essence, blueberry essence, kiwi essence, strawberry essence, raspberry essence, cherry essence, plum essence, pineapple essence, and apricot essence, natural mixed berry flavor, citric acid, malic acid, vanilla, vanillin, cocoa, chocolate, and menthol. In addition, the flavors may be selected from one or more of the group consisting of anise oil, cinnamon oil, peppermint oil, oil of wintergreen, clove oil, bay oil, anise oil, *eucalyptus* oil, thyme oil, cedar leave oil, oil of nutmeg, oil of sage, oil of bitter almonds, *cassia* oil, lemon oil, orange oil, lime oil, grapefruit oil, grape oil and combinations thereof.

Natural flavors, artificial flavors or mixtures thereof include mint (such as peppermint or spearmint), menthol, cinnamon, vanilla, artificial vanilla, chocolate, artificial chocolate or bubblegum. Natural fruit flavors, artificial fruit flavors or mixtures thereof include, but are not limited to, cherry, grape, orange, strawberry or lemon. Flavour enhancers include, but are not limited to, citric acid. Although flavoring agents are generally provided as a minor component of the formulation, the addition of at least one flavoring agent is preferred. However, up to two flavoring agents may generally be employed.

The taste masking composition may further comprise an effective amount of a sweetener, at least one flavoring agent, and an artificial sweetening agent.

Optional sweetening agents include, but are not limited to, sugar sweeteners such as monosaccharides, disaccharides and polysaccharides. Examples of suitable sugar sweeteners include, but are not limited to, xylose, ribose, glucose, mannose, galactose, fructose, dextrose, sucrose, maltose, partially hydrolysed starch (such as maltitol syrup) or corn syrup, and sugar alcohols such as sorbitol, xylitol, mannitol, glycerin and combinations thereof. Artificial sweeteners include, but are not limited to, aspartame, acesulfame potassium, cyclamate, saccharin, saccharin sodium, sucralose and mixtures thereof.

The amount of additional sugars, optional and artificial sweetener used in the formulation will vary depending on the degree of sweetness and palatability desired.

The liquid formulations according to the disclosure are preferably formulated with a certain degree of viscosity, which may be imparted by the date material. Alternatively, additional viscosity enhancing agents may be included to achieve the optimum viscosity, taste masking and desired physical and/or chemical characteristics throughout product shelf life.

Examples for viscosity agents are poly(vinylpyrrolidone); polyvinyl alcohol; methylcellulose, hydroxypropyl methylcellulose, sodium carboxymethylcellulose, and mixtures thereof; sodium alginate; polyacrylamides; polyacrylic acids; collagen; polyethylene glycol; polysaccharides and carbohydrates such as starch, cellulose, dextrans and derivatives; thixotropic media; and the like. Other viscosity agents include natural gums such tragacanth, acacia or xanthan gum, guar gum, and gelatin, as well as clays such as veegum, bentonite, and hectorite.

In another embodiment a preservative system for is used as an oral liquid such as the liquid formulations of the disclosure, and this may be selected from those conventionally employed in oral medicines. These usually consist of benzoic acid, sodium benzoate, potassium sorbate, ascorbic acid, sorbic acid, domiphen or other suitable preservatives and their mixtures.

As the liquid formulations of the disclosure may be thermodynamically unstable dispersed systems, in which the solid particles of the internal phase tend to aggregate and form sediment, the use of a coadjuvant may be required to improve dispersion, viscosity and other aspects so that a stable product is obtained.

An effective quantity of a wetting agent may be required if relatively insoluble drugs or ingredients are present in the composition. Such wetting agents may be selected from the group consisting of surface active agents, (e.g. anionic, non-ionic and cationic surfactants), glycerol, propylene glycol, liquid polyethylene glycols, sorbitol and mixtures thereof.

The formulation may also contain demulcents additional to the date material, such as liquorice (*Glycyrrhiza*), to further enhance the demulcent properties of the formulation.

In another embodiment of the disclosure the date composition may be taken on an empty stomach. Preferably, the date composition is taken when a patient has not ingested food for more than 12 hours. More preferably, the date composition is taken during the morning hours of the day when a patient has not ingested food for more than 12 hours.

In another embodiment the date composition is administered to a subject for a time period in the range of 12 hours to 30 days before the subject is exposed to a biological venom or chemical toxin. Preferably the subject is administered the date composition for a time period of 24 hours prior to being exposed to a biological venom or chemical toxin. More preferably, the date composition is administered to a patient so that at least 21.7 g of the date composition is present in the subject.

In another embodiment the date composition is effective for a time period of 12 hours to 48 hours once at least 21.7 g of the composition is present in the patient.

One embodiment describes a method for administering a homogenized composition comprising the fruit *Phoenix dactylifera* in an amount effective to prophylactically inhibit a biological toxin or a chemical toxin from causing harm to a mammal, comprising: administering the homogenized composition in an amount of at least 0.4 g of date/kg of the human.

The method further comprises: homogenizing the fruit *Phoenix dactylifera*.

In another embodiment the *Phoenix dactylifera* is the Ajwah date.

In another embodiment composition is administered in an amount effective to prophylactically prevent harm from one or more biological toxins selected from the group consisting of spider venom, snake venom, scorpion venom, jellyfish venom, bee venom, ant venom, termite venom, honeybee venom, wasp venom, and poison dart frog venom. In another embodiment the composition is administered in an amount effective to prophylactically prevent harm from one or more chemical toxins selected from the group consisting of carbon tetrachloride, strychnine, cyanide, lead, arsenate, and mercury.

In another embodiment the composition is administered orally in solid or liquid form.

In another embodiment the composition is administered in the liquid form and wherein the homogenized composition includes syrup, artificial sweetening agents or natural fruit flavoring agents.

In another embodiment the patient is administered the composition only if no food has been ingested for a time period of 12 hours.

Another embodiment describes a method of inhibiting a biological toxin or a chemical toxin in a subject, comprising: administering a homogenized composition comprising a date fruit in an amount of at least 0.4 g of date/kg of the subject; wherein the administering occurs at a time period of at least 12 hours before the subject is exposed to the biological toxin or the chemical toxin.

In another embodiment the subject is any mammal including a dog, horse, or human.

In another embodiment the method further comprises homogenizing the fruit *Phoenix dactylifera*.

In another embodiment the *Phoenix dactylifera* is the Ajwah date.

In another embodiment the composition is administered in an amount effective to inhibit one or more biological toxins selected from the group consisting of spider venom, snake venom, scorpion venom, jellyfish venom, bee venom, ant venom, termite venom, honeybee venom, wasp venom, and poison dart frog venom.

In another embodiment the composition is administered in an amount effective to inhibit one or more chemical toxins selected from the group consisting of carbon tetrachloride, strychnine, cyanide, lead, arsenate, and mercury.

In another embodiment the composition is administered orally in solid or liquid form.

In another embodiment the composition is administered in the liquid form and wherein the homogenized composition includes syrup, artificial sweetening agents, or natural fruit flavoring agents.

In another embodiment the composition is administered in an amount in the range of 0.70 g/kg-0.95 g/kg to a human.

EXAMPLES

In the following Example 1, the date composition is presented below.

Date Composition

| Carbohydrates | 30% |
|---|---|
| Minerals | 13% |
| Proteins | 40% |
| Fatty Acids | 10% |
| Moisture Content | 5% |
| Ash | 2% |

The Ajwah dates are mixed with an aqueous solution to form a first mixture. The first mixture is then passed through a blender or homogenizer until at least 95% of the date material is homogenized in the aqueous solution. The following ingredients may also be added to the first mixture including but not limited to syrups, flavoring agents, ibuprofen or any other anti-inflammatory agent, citric acid, preservatives, or any other acceptable form of a date composition.

Prior to forming the composition, the moisture content of the dates is used to obtain a moisture balance and the dates are heated at a temperature in the range of 90-150° C., 95-140° C., or 100-130° C. for a time period in the range of 30-60 minutes, 35-55 minutes, or 40-45 minutes. Preferably the dates are heated at a temperature of 110 for 45 minutes.

The date composition is tested against venoms derived from the following animals including but not limited to *Naja Melanoleuca, Bitis Gabonica, Bitis Arietans*, Narrowbanded krait (*Bungarus multicinctus*), Cobra snake (*Naja naja atra* Chinese Cobra), King cobra (*Ophiophagus hannah, Agkistrodon acutus, Vipera russelli, Siamensis* smith, *Bungarus fasciatus* Schneider, *Agkistrodon blomhoffi* Boie, *Trimeresurus mucroquamatus, Trimerurus stejnegeri* Schmidt, *Acanthopis laevis, Hadogenes troglodytes, Leiurus quinquestriatus*.

The date composition is also tested against chemical toxins including carbon tetrachloride, strychnine, cyanide, lead, arsenate, and mercury.

The date composition of Example 1 is effective for up to 12 hours before exposure to the toxins or venoms described above.

Each venom listed above was tested separately in 10 rats pretreated via gastric gavage (intubation) with the date composition in a dose of 0.4 g/kg. Each rat was then injected with 0.1 microliter of a venom from the venoms listed above.

Each chemical toxin was tested separately in 10 rats pretreated via gastric gavage (intubation) with the date composition in a dose of 0.4 g/kg. Each rat was then injected with the following volumes of each chemical toxin: carbon tetrachloride in a dose of 2.5 ml/kg to be administered orally to the rats, strychnine in a dose of 0.1 microliter to be administered via intraperitoneal injection, cyanide in a dose of 0.1 microliter to be administered via intraperitoneal injection, lead in a dose of 300 ppm to be administered orally, arsenate in a dose of 70 ppm to be administered orally, and mercury in a dose of 4 mg/kg to be administered orally.

After the venom and chemical toxins were injected, mortality rates and organ functions (including liver and kidney function) were observed. Kidney and liver function was measured by performing a kidney function test and a liver function test in all of the surviving rats after being subjected to both the date composition and the toxin. The kidney function test includes both a creatinine test and a blood urea nitrogen (BUN) test. The BUN test performed in all surviving rats that were exposed to either venom or chemical toxins demonstrated that the amount of nitrogen in the blood derived from urea is in the range of 10-20 mg/dL. The range of 15-21 mg/dL of nitrogen in the blood derived from urea demonstrates stable and normal kidney function in rats. A normal range of nitrogen in the blood derived from urea in rats is 15-21 mg/dL and a normal range of nitrogen in the blood derived from urea in humans is 10-20 mg/dL.

The creatinine test performed in all surviving rats that were exposed to either venom or chemical toxin demonstrated that the amount of creatinine in the blood is in the range of 0.2-0.8 mg/dL. The range of 0.2-0.8 mg/dL of creatinine in the blood demonstrates stable and normal kidney function in rats. A normal range of creatinine in the blood in rats is 0.2-0.8 mg/dL and a normal range of creatinine in the blood in humans is 0.6-1.3 mg/dL.

The liver function test includes an alanine transaminase (ALT) test, an aspartate aminotransferase (AST) test, and a total bilirubin (TBiI) test. The ALT test performed in all surviving rats that were exposed to either venom or chemical toxin demonstrated that the amount of alanine transaminase in the blood is in the range of 17.5-30.2 U/L. The range of 17.5-30.2 U/L of alanine transaminase in the blood demonstrates stable and normal liver function in rats. A normal range of alanine transaminase in the blood in rats is 17.5-30.2 U/L and a normal range of alanine transaminase in the blood in humans is 10-40 U/L for males and 7-35 U/L for females.

The AST test performed in all surviving rats that were exposed to either venom or chemical toxin demonstrated that the amount of aspartate aminotransferase in the blood is in the range of 45.7-80.0 U/L. The range of 45.7-80.0 U/L of aspartate aminotransferase in the blood demonstrates stable and normal liver function in rats. A normal range of aspartate aminotransferase in the blood in rats is 45.7-80.0 U/L and a normal range of aspartate aminotransferase in the blood in humans is 14-20 U/L for males and 10-36 U/L for females.

The TBiI test performed in all surviving rats that were exposed to either venom or chemical toxin demonstrated that the amount of total bilirubin in the blood is in the range 0.2-0.55 mg/dL. The range of range 0.2-0.55 mg/dL of total bilirubin in the blood demonstrates stable and normal liver function in rats. A normal range of total bilirubin in the blood in rats is range 0.2-0.55 mg/dL and a normal range of total bilirubin in the blood in humans is 0.0-1.0 mg/dL.

Every single rat injected with a different venom and the same date composition survived exposure to the venom and chemical toxins. The results are presented below.

Test Results Against Venom of Example 1

| Number of Rats | Dosage of date composition | Dosage of venom (In each rat) | Number Dead | Number Survived |
|---|---|---|---|---|
| 10 | 0.4 g/kg | 0.1 microliter intramuscular injection | 0 | 10 |
| 10 | 0 g/kg | Control group | 10 | 0 |

Test Results Against Chemical Toxins of Example 1

| Number of Rats | Dosage of Date Composition | Dosage of Chemical Toxin | Method of administering | Number Dead | Number Survived |
|---|---|---|---|---|---|
| 10 | 0.4 g/kg | Carbon tetrachloride- 2.5 mL/kg | Oral | 0 | 10 |
| 10 | 0.4 g/kg | Strychnine- 0.1 microliter | Intraperitoneal injection | 0 | 10 |
| 10 | 0.4 g/kg | Cyanide-0.1 microliter | Intraperitoneal injection | 0 | 10 |
| 10 | 0.4 g/kg | Lead-300 ppm | Oral | 0 | 10 |

-continued

| Number of Rats | Dosage of Date Composition | Dosage of Chemical Toxin | Method of administering | Number Dead | Number Survived |
|---|---|---|---|---|---|
| 10 | 0.4 g/kg | Arsenate-70 ppm | Oral | 0 | 10 |
| 10 | 0.4 g/kg | Mercury-4 mg/kg | Oral | 0 | 10 |
| 10 | 0 g/kg | Control group | Control group | 10 | 0 |

Extrapolation to a human patient was performed according to the physiologically based pharmacokinetic (PBPK) model of Gelman (Gelman, A.; Bois, F. Y., Jiang, J. (1996). "Physiological pharmacokinetic analysis using population modeling and informative prior distributions". *Journal of the American Statistical Association* 91: 1400-1412—incorporated herein by reference in its entirety). Extrapolation to a human patient demonstrates that the effective dosage to be administered to a human in an amount effective to prevent a patient from harmful exposure to the chemical toxins or venoms described above is 0.8 g of date composition/kg of human.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A method for treating a human suffering from a spider venom, a snake venom, a scorpion venom, a jellyfish venom, a bee venom, an ant venom, a termite venom, a honeybee venom, a wasp venom, a poison dart frog venom, carbon tetrachloride poisoning, strychnine poisoning, cyanide poisoning, arsenate poisoning, or mercury poisoning comprising administering to said human a therapeutically effective amount of an Ajwa date to effectively treat the human suffering from a spider venom, a snake venom, a scorpion venom, a jellyfish venom, a bee venom, an ant venom, a termite venom, a honeybee venom, a wasp venom, a poison dart frog venom, carbon tetrachloride poisoning, strychnine poisoning, cyanide poisoning, arsenate poisoning, or mercury poisoning.

2. The method of claim 1, wherein the Ajwa date is homogenized.

3. The method of claim 2, wherein the therapeutically effective amount is at least 0.4 g of Ajwa date/kg of the human.

4. The method of claim 3, wherein the therapeutically effective amount is 0.4-0.6 g of Ajwa date/kg of the human.

* * * * *